United States Patent [19]

Kissinger et al.

[11] Patent Number: 5,792,095
[45] Date of Patent: Aug. 11, 1998

[54] OCCLUDING COLLECTOR, SYSTEM AND METHOD

[75] Inventors: Jacob T. Kissinger, 144 Joan Dr., Collegeville-Trappe, Pa. 19426; Michael A. Schnell, Glenmoore; Eric M. Garver, Wayne, both of Pa.

[73] Assignee: Jacob T. Kissinger, Collegeville-Trappe, Pa.

[21] Appl. No.: 673,975

[22] Filed: Jul. 1, 1996

[51] Int. Cl.$^6$ ............................................. A61M 5/00
[52] U.S. Cl. ......................................... 604/9; 604/284
[58] Field of Search ............................ 604/8, 9, 10, 284

[56] References Cited

U.S. PATENT DOCUMENTS

| H85 | 7/1986 | Shortsleeve | 604/284 |
|---|---|---|---|
| 2,587,910 | 3/1952 | Shulman | 128/2 |
| 3,392,722 | 7/1968 | Jorgensen | 128/1 |
| 3,515,124 | 6/1970 | Gurchot | 128/1 |
| 3,833,940 | 9/1974 | Hartenbach | 3/1 |
| 4,263,917 | 4/1981 | Moss | 128/1 |
| 4,547,187 | 10/1985 | Kelly | 604/49 |
| 4,734,094 | 3/1988 | Jacob et al. | 604/284 |
| 5,213,575 | 5/1993 | Scotti | 604/95 |
| 5,224,931 | 7/1993 | Kumar | 604/51 |

OTHER PUBLICATIONS

Barringer et al., "Chronic Biliary Sampling Via a Subcutaneous System in Dogs", *Laboratory Animal Science*, 1982.
Madrid et al., "use of a Bidirectional Cannula to Study Biliary Secretion in Conscious Dogs", *Laboratory Animals*, 1983.
Jacob et al., "A Double Ballooned Inflatable and Collapsible T Tube for Selecting Proximal or Distal Cholangiography", *Surgery, Gynecology & Obstetrics*, 1988.
Faidley et al. "A Surgical Model for Studying Biliary Bile Acid and Cholesterol Metabolism in Swine," *Laboratory Animal Science*, 1991.

*Primary Examiner*—Robert A. Clarke
*Attorney, Agent, or Firm*—Michael F. Petock, Esq.

[57] ABSTRACT

An occluding collector is a housing with two tubular members adapted to be inserted into a duct carrying a biological fluid. A biological fluid passageway is provided within the housing between the two tubular members. A flexible member is operable to selectively close or open the biological fluid passageway in response to a fluid operating pressure in a catheter. In a preferred embodiment, the flexible member is a diaphragm which is movable to a convex condition for closing the biological fluid passageway and retaining the closed condition in the absence of sustained operating fluid pressure. The diaphragm may be moved to a concave condition for opening the biological fluid passageway in response to suction or partial vacuum created by retraction of some operating fluid. The diaphragm also retains its concave or open condition until again acted upon by the operating fluid. When the biological passageway is closed, the biological fluid may be drained or collected through a second catheter. A third catheter may be provided, which communicates with the other tubular member, to act as a flush or dosing catheter. A method of fabricating the occluding collector is disclosed. A method of using the catheter to collect bile in animals wherein the system is totally implanted without any transdermal catheters is disclosed.

26 Claims, 4 Drawing Sheets

OCCLUDING COLLECTOR, SYSTEM AND METHOD

FIELD OF THE INVENTION

The present invention relates to an occluding collector, system and method. More particularly, the present invention relates to an occluding collector for occluding a duct carrying a biological fluid and collecting the biological fluid. The present invention includes a system and method of collecting such biological fluids and a method of making the collector.

BACKGROUND OF THE INVENTION

Efforts have been made in the past to devise apparatus and systems for the collection of bile from dogs and other animals on a continuous basis for use in medical research and related activities. For example, see Barringer et al., "Chronic Biliary Sampling Via a Subcutaneous System in Dogs", *Laboratory Animal Science*, 1982 and Madrid et al., "Use of a Bidirectional Cannula to Study Biliary Secretion in Conscious Dogs", *Laboratory Animals*, 1983.

The present invention provides significantly improved apparatus for a system and method for biliary sampling in animals and provides an occluding, collecting, dosing or flushing apparatus useful both in medical research and in human treatment applications.

SUMMARY OF THE INVENTION

The present invention provides an apparatus, system and method which is useful in laboratory animal research as well as in other human treatment applications. The present invention provides an apparatus of small dimensions, which preferably may be made on the order of about 3 centimeters overall length and may be made as small as 2 centimeters or smaller, which is totally implantable and causes minimal trauma or physiological disruption to the animal or patient. The apparatus of the present invention, in a preferred embodiment, provides a diaphragm which may be operated to a closed position by the application of pressure and will remain in the closed position until the diaphragm is drawn to the open position by the withdrawal of a fluid (gas or liquid) which creates a suction force on the diaphragm.

In laboratory use, the system of the present invention has provided a more physiologically normal animal model than other catheters. This is shown by the fact that when the system of the present invention is implanted in an animal, the serum enzyme levels related to liver and biliary system function return substantially to normal postoperatively. These enzymes include alanine aminotransferase, gamma glutamyltransferase, and alkaline phosphatase. Other models, both implantable and exteriorized, have not consistently demonstrated the same results, that is return of the serum enzyme levels to substantially normal postoperatively.

Further advantages of the occluder catheter include, in a preferred embodiment, that the flexible concave/convex diaphragm holds its open or closed position on its own. This makes it easier to operate and use over extended periods of time since no extra pressure or vacuum is needed to keep the diaphragm in one position. Further, a distal access catheter allows for infusion into the system whether or not bile collection is occurring. This catheter provides the capability for flushing obstruction and for dosing drugs or medicaments on the distal side of the occluder.

Where the apparatus is used to collect bile, with the diaphragm closed to block the normal passage of bile through the common bile duct to the duodenum, all of the bile is collected. This "quantitative collection" provides a valuable model for drug absorption, distribution and excretion studies. A closed diaphragm would also allow unidirectional infusion for purposes such as duodenal dosing or radiography.

The apparatus in accordance with the concept of the present invention includes a housing having a biological passageway between and connected to a first and second tubular members adapted to be inserted into a duct carrying a biological fluid. A flexible member is mounted within the housing and is deflectable in response to pressure of a fluid (gas or liquid) to close the biological passageway. A catheter is connected to the housing for applying the operating fluid for deflection of the flexible member and a second catheter is provided wherein a lumen of the second catheter is in communication with a lumen of one of the tubular members.

In a preferred embodiment, the flexible member is in the form of a diaphragm which is deflectable to a convex condition in response to pressure of the operating fluid to close the biological fluid passageway. The diaphragm is retractable to a concave condition in response to suction of the operating fluid to open the biological fluid passageway. The diaphragm remains in the convex condition once pressure has been applied until a suction force is applied to the diaphragm to move it to its open concave condition. In other words, the diaphragm has two stable conditions, one being convex (closed) and the other being concave (open).

A third catheter may be provided for flushing or dosing. The lumen of the third catheter is in communication with the lumen of the other tubular member which connects into the duct. Such flushing or dosing would most typically take place when the flexible member or diaphragm is in the condition closing the biological fluid passageway. However, this would be determined by the particular laboratory or medical treatment application being undertaken.

Preferably, the housing, tubular members, catheter and diaphragm would all be constructed of medical grade silicone. In certain applications, a layer of material, such as polyurethane, having a surface of low adhesion may be provided to act as the surface against which the flexible member or the diaphragm comes in contact upon being deflected in response to the pressure of the operating fluid. This prevents the flexible member or diaphragm from adhering in the closed position and facilitates the opening of the occluder by a low level of suction pressure.

The diaphragm or flexible member may be of various shapes in addition to round or hemispherical, some examples are oval, rectangular, including square, cylindrical or any other suitable shape. Additionally, a radiopaque substance may be incorporated into the occluder, such as at various points in the housing, in the tubular members or in both. The radiopaque substance may be a metal, such as stainless steel, incorporated within the body of the tubular members or other locations in the housing, or may be filler material disbursed throughout the silicone to provide radiopacity.

There is also disclosed a method of collecting bile in an animal wherein longevity of the animal is promoted with normal or near normal serum enzymes. In accordance with this method, a housing having a biological passageway between and connected to a first and second tubular members is implanted in the common bile duct with the first and second tubular members inserted into the bile duct. Selective operation of a flexible member mounted within the housing to open and close the biological passageway is accomplished by utilizing pressure of an operating fluid delivered via a catheter from a subdermal access port. The bile is collected via a second catheter which communicates with a lumen of one of the tubular members closest to the gall bladder of the animal. The second catheter is in communication with a second subdermal access port.

Additionally, the invention comprises a method of constructing an apparatus of the type described including the steps of molding a diaphragm of silicone material on the end of a mold having a convex surface, molding a polyurethane cap over the silicone diaphragm, molding a cap portion of a housing over the layer of polyurethane, forming holes at two locations through the housing and cap, attaching a first and second tubular members to communicate with the holes, attaching a lower portion of the housing and a catheter to the housing such that the catheter lumen is in communication with one surface of the diaphragm and forming a catheter to communicate with one of the tubular members.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

DETAILED DESCRIPTION OF THE PREFERRED EMBODIMENTS

Figures 1, 7:
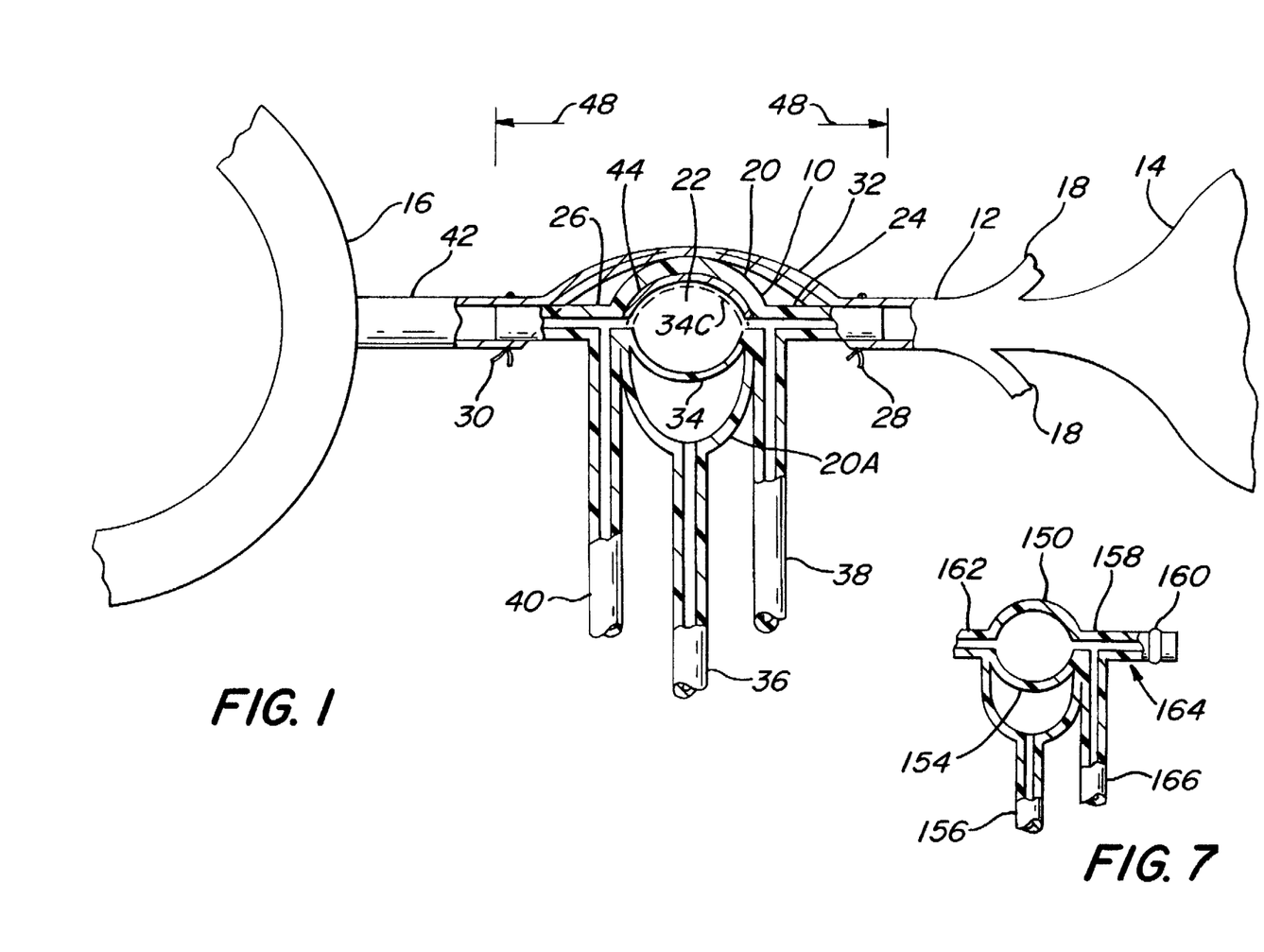
FIG. 1 is an elevation view, partially in cross-section, of an occluding collector in accordance with the present invention implanted in a common bile duct.
FIG. 7 is an elevation view, partially in cross-section, of another embodiment of an occluding collector illustrating suturing rings on the tubular members which are inserted into a biological fluid carrying duct.

Referring now to the drawings in detail, wherein like numerals indicate like elements, there-is shown in FIG. 1 an occluding collector 10 mounted in a duct 12 which may carry a biological fluid. In the specific example illustrated in FIGS. 1, 3A and 3B, duct 12 is the common bile duct which carries a biological fluid in the form of bile from primarily the gall bladder 14 to the duodenum 16. Ducts 18 are hepatic ducts which also empty into the common bile duct 12.

Occluding collector 10 includes a housing or shell 20 having a biological fluid passageway 22 between a first tubular member 24 and a second tubular member 26.

The tubular members 24 and 26 are inserted or mounted into duct 12 carrying the biological fluid, bile. This may be accomplished in various ways. As illustrated in FIG. 1, a pair of spaced incisions or ostomies are made in duct 12 into which tubular members 24 and 26 are inserted. Tubular members 24 and 26 are preferably secured in duct 12 by a pair of tied ligatures 28 and 30, respectively. Preferably, rather than dividing duct 12, portion 32 of duct 12 is merely flattened and folded around housing 20.

It is understood that the occluding collector of the present invention may be utilized in various other ways. The duct to which it is inserted may be merely divided. Furthermore, the occluding collector may be mounted closer to the duodenum. Furthermore, the occluding collector of the present invention has uses in various other applications both in animal research and in human applications including uses in various ducts such as urinary ducts, lymphatic ducts, veins, -arteries and other ducts which may carry biological fluids as well as uses in applications such as cholangiography cerebro-peritoneal shunts and other applications which will be obvious to those skilled in the medical and research arts.

Referring further to the structure of occluding collector 10, there is shown a flexible member 34 which is shown in its open position allowing passage of biological fluid through first tubular member 24, biological passageway 22 and second tubular member 26. Flexible member 34 is deflectable by an operating fluid applied to diaphragm 34 via a first catheter 36 to cause diaphragm 34 to move to its closed position, which is illustrated in dotted outline form at 34C. Operating fluid supplied via catheter 36 may be any suitable gas or liquid including, but not limited to, air, nitrogen or saline solution.

A second catheter 38 is provided with the lumen of catheter 38 being in communication with the lumen of tubular member 24. Catheter 38 functions as a collector or drain for biological fluid when flexible member 34 is in the closed position represented by 34C. In the specific application illustrated in FIG. 1, catheter 38 would collect or act as a drain for bile from the common bile duct.

A third catheter 40 may be provided, the lumen of which would be in communication with the lumen of the other tubular member 26. Catheter 40 may be utilized to flush the distal end 42 of the common bile duct. Other uses of catheter 40 include flushing the diaphragm area and infusing material towards the duodenum.

In a preferred embodiment, flexible member 34 is preferably constructed in the form of a diaphragm wherein it retains its concave condition in the open position or in the closed position 34C (convex condition) in the absence of a pressure or force acting upon it. For example, when operating fluid is applied to the lower face of diaphragm 34 it is forced to its closed position 34C and retains that closed position without the necessity of applying a constant operating fluid pressure in the lower half of housing 20 referred to by the numeral 20A. When operating fluid is withdrawn from lower housing 20A via catheter 36, a suction or partial vacuum is applied to the lower side of diaphragm 34C causing it to be retracted to its open position shown at 34. Diaphragm 34 will remain in its retracted or open position without the maintenance of a continuous suction or partial vacuum on diaphragm 34. Accordingly, the occluder of the present invention provides the advantage that once operated to the open or closed position, there is no necessity to maintain a constant pressure or suction force on the diaphragm in order to maintain its condition. However, the maintenance of pressure or suction on the diaphragm is within the spirit and scope of the present invention.

In an optional, but presently preferred embodiment of the invention, the innersurface of the upper portion of housing 20 of occluding collector may be provided with a layer of material 44 against which flexible member 34 comes-in contact upon being deflected to the closed position 34C. Layer 44 is preferably a material having a surface of low adhesion, such as polyurethane. The polyurethane layer or cap 44 prevents adhesion or sticking of the flexible member or diaphragm 34 and therefore ensures that diaphragm 34 may be moved to its open position with a minimal suction or partial vacuum being applied through catheter 36. However, polyurethane layer 44 is not deemed to be essential in all applications.

Occluding collector 10 may be constructed as a unitary structure completely of medical grade silicone, except for the polyurethane layer 44. Catheters 36, 38 and 40 may be similarly constructed of medical grade silicone. However, it is understood that other suitable materials may be utilized in practicing the present invention. Furthermore, the entire occluding collector 10 is of a relatively small dimension, the dimension from the outer end of tubular member 24 to the outer end of tubular member 26, as illustrated by the dimension arrows 48, preferably may be approximately three centimeters but it may be two centimeters or less. The small dimensions of the device enable it to be better tolerated by an animal, including humans.

Figure 3A:
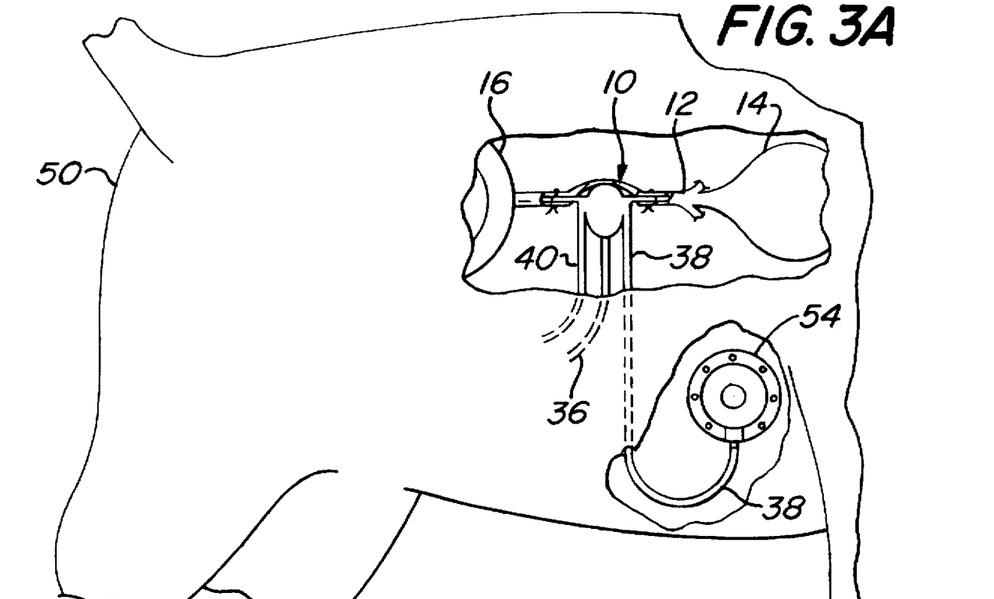
FIG. 3A and 3B illustrate an occluding bile collection system in accordance with the present invention implanted in a dog.
Figure 3B:
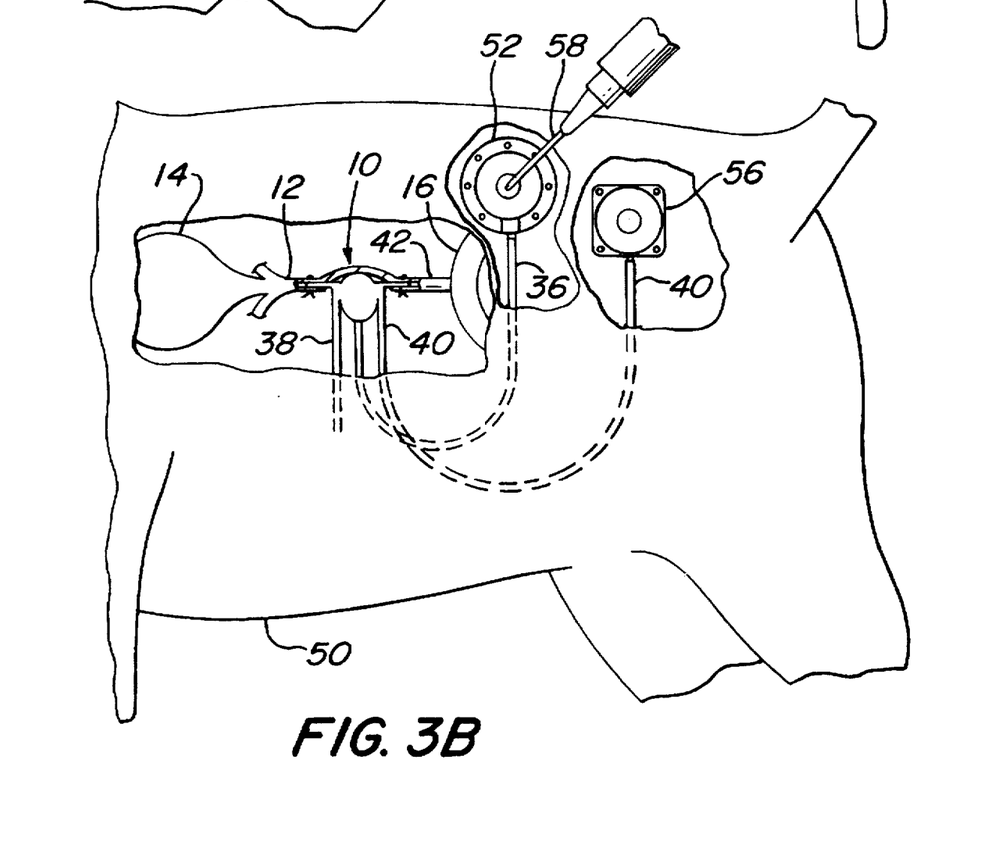

Referring now to FIGS. 3A and 3B, the occluding collector 10 described in FIG. 1 is shown implanted in a dog 50. As illustrated in FIGS. 3A and 3B, first catheter or operating catheter 36 is connected at its distal end to a subdermally implanted access port 52. The second catheter or drain or collecting catheter 38 is connected at its distal end to subdermal access port 54. The distal end of catheter 40 is connected to subdermal access port 56. Subdermal access ports, such as those illustrated at 52, 54 and 56 are commercially available. They are available in differing sizes and shapes, two such shapes being illustrated at 52 and 56. Access ports, such as access port 52, are commercially available from Access Technologies, a division of Norfolk Medical, 7350 N. Ridgeway, Skokie, Ill., 60076. Access ports are commercially available for use in both animals in research and for human applications, including dosing for chemotherapy and the like. Access port 56 illustrates one commercially available access port which utilizes a titanium housing of a type commonly used in human therapeutic applications.

As illustrated in FIG. 3B, the access port when implanted under the skin of the animal, including humans depending upon the particular application, is accessed by a (hypodermic) syringe 58 which is utilized to pierce the skin and enter the lumen of the access port. Any suitable type of needle may be used to access the port. In this manner, fluids may be injected into the system via the access port or withdrawn from the system via the access port. As illustrated in FIG. 3B, syringe 58 may be utilized to operate the diaphragm or flexible membrane 34 of the occluding collector 10. If the syringe 58 is utilized to inject a fluid (gas or liquid) into access port 52, the pressure of the operating fluid so injected is transmitted via catheter 36 to the inside of housing 20A applying pressure to diaphragm 34 causing it to close to position 34C as shown in FIG. 1. If fluid is withdrawn from access port 52 by syringe 58, a negative pressure, suction or partial vacuum is applied to the underside of the diaphragm or flexible membrane 34C causing it to be retracted to its open position 34 as shown in FIG. 1. The bile collection system as illustrated in FIGS. 3A and 3B may be used in laboratory animals, such as the dog illustrated, to collect bile from the bile duct of conscious, freely moving animals. At will of the researcher, the researcher may temporarily stop the natural flow of bile through bile duct 12 and prevent it from entering the duodenum. All bile produced by the animal may be collected via catheter 38 and withdrawn via access port 54 using a suitable syringe. Systems other than a syringe may be used to collect bile from the access port. For example, a needle with an attached catheter may lead (a) to a collection vessel which may be protected in a jacket on the animal, or, (b) via a tethering line to a collection vessel mounted outside the animal's cage. Further, by use of catheter 40 and access port 56, the distal section 42 of the common bile duct may be flushed (with the occluder 10 in the closed condition) or catheter 40 may be utilized for selective dosing of the duodenum with medicaments, controlled amounts of bile, drugs or other fluids as desired.

A totally implanted system as illustrated in FIGS. 3A and 3B is better tolerated by the animals than a system where there are open wounds which may become infected. Furthermore, with the system as illustrated, there are no exteriorized catheters which may be damaged by the animal. The use of a totally implanted system as illustrated in FIGS. 3A and 3B provides the animals with a longer functional lifespan. This should result in a decrease in the number of animals needed and provide a more scientifically valid model since the same animal may be utilized as its own control as well as on additional studies, thereby eliminating inter-animal variability. Further, a totally implanted system as illustrated provides a less labor intensive model for support staff since there are no protective jackets or bandages on the animal to be maintained and no open skin wounds to keep clean. A longer functional lifespan for the laboratory animal also minimizes the overall number of surgical procedures required to maintain a working colony of animals.

Figure 2:
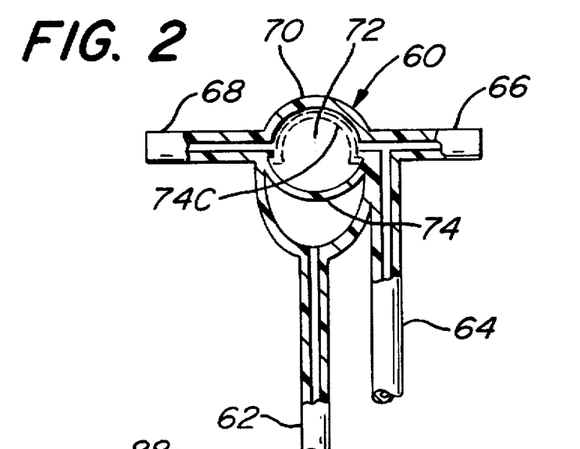
FIG. 2 is an elevation view, partially in cross-section, of another embodiment of the present invention.

Referring now to FIG. 2, there is shown another embodiment of the present invention wherein an occluder 60 is provided with an operating catheter 62 and an additional catheter 64, the lumen of which communicates with the lumen of one of the tubular members, namely tubular member 66. In most applications, it is anticipated that catheter 64 would be utilized as a drain or collecting catheter when occluder 60 is in the closed condition. However, it is understood that occluder 60 could be utilized to occlude a duct with catheter 64 being utilized for dosing, flushing or infusing contrast media. Furthermore, it is understood throughout the specification and claims that the term duct is used broadly to specify any living tissue structure for carrying biological fluids including veins, lymphatic ducts or vessels, ureters, vessels or the like in any type of animal, including the human animal.

Referring further to FIG. 2, there is shown a second tubular member 68 mounted to or formed as a part of housing or shell 70. The inside of housing 70 forms a biological fluid passageway 72 which may be closed by flexible member 74 when it is moved into the closed position as illustrated in dotted outline at 74C.

As described with respect to occluding collector 10 in FIG. 1, the entire occluding collector 60 as well as the catheters may be constructed of medical grade silicone. In both of the embodiments illustrated in FIGS. 1 and 2, the tubular members 24 and 26 of FIG. 1 as well as the tubular members 66 and 68 of FIG. 2 may be aligned. However, it is understood that it is not necessary that the tubular members be aligned, and they may be positioned on some other angle, such as 120° apart. This may provide advantages in certain applications, particularly where it is desirable to insert the occluder in a duct with incisions being less than 3 centimeters apart or for other reasons. In any event, independent of the alignment or degree of nonalignment of the input and output tubular members, flexible member or diaphragm 34 or 74 when operated will close the biological fluid passageway within the housing.

It is further noted that the embodiment of FIG. 2 does not utilize any low adhesion layer or cap within housing 72 when diaphragm 74 is in the closed position 74C. This may be particularly the case where the occluder 60 may be made by injection molding or a similar process.

Referring now to FIGS. 4A, 4B, 4C and 4D, there is illustrated various steps in accordance with a presently preferred method of constructing an occluding collector in accordance with the present invention. It is understood that other methods of constructing an occluding collector in accordance with the present invention may be utilized and methods such as injection molding may become a preferred method in the future.

Figure 4A:
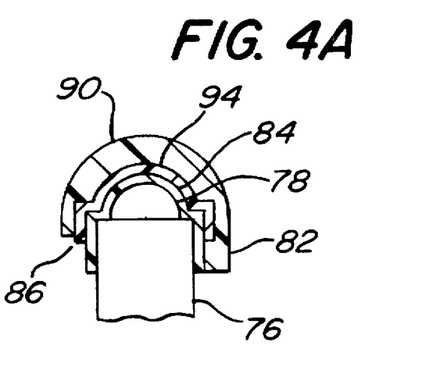
FIGS. 4A through 4D are elevation views, partially in cross-section, which illustrate steps in one method of fabricating an occluding collector in accordance with the present invention.

As presently preferred, as illustrated in FIG. 4A, the method of fabrication may be started with a teflon rod 76, approximately 4 millimeters in diameter where one end is rounded to a convex or dome shape 78 having a diameter of approximately 2.4 millimeters and a dome height of approximately 1.4 millimeters. The ridge around the dome is best shown at 80 in FIG. 4B and this has a dimension of approximately 0.8 millimeters. Molds of other types of materials which allow the diaphragm to be readily removed or peeled off may be used, such as commercially available Delrin.

Mold 76 may be dip coated three times in a 50% solution of SILASTIC™ medical adhesive silicone type A paste dissolved in a xylene solution. The medical adhesive silicone is preferably cured under a heat lamp at approximately 115° F. However, it may be cured at room temperature. The final thickness of the cured silicone diaphragm 84 is approximately 0.32 millimeters on top of the dome 78 and approximately 1.25 millimeters on the sides of the mold base. This concludes the formation of diaphragm 84.

To form the layer of material having a surface of low adhesion 94 of polyurethane, the mold is dip coated two times in a 17% solution of SURETHANE segmented polyether polyurethane dissolved in N,N-Dimethylacetamide. The segmented polyether polyurethane is cured under heat lamps to a thickness of approximately 0.10 millimeters. The segmented polyether polyurethane layer or cap 94 is then trimmed around the mold at a distance of approximately 1 millimeter below the dome's ridge edge.

Figure 4B:
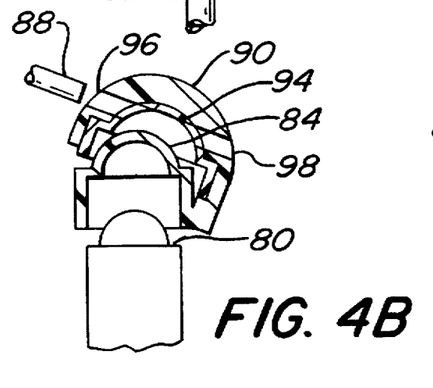

The polyurethane layer 94 is then coated with a layer of approximately 2 millimeters thickness of medical adhesive silicone type A paste. The silicone paste is also applied over the edge of the polyurethane layer 94 and on top of the underlying silicone around half of the circumference as indicated at 82. Please note that the area 86 is not covered at this time. The raising of the housing 90 and the polyurethane layer 94 in the next step is illustrated in FIG. 4B.

The thickened silicone housing or shell 90 with the attached underlying polyurethane layer 94 is flipped or lifted back. A stainless steel or other suitable punch 88 is used to make two holes 96 and 98, preferably 180° apart through the silicone housing 90 and the polyurethane layer 94. However, as discussed above, these holes may be made at some other angle depending upon the particular application desired. However, as presently preferred, these are made 180° apart. These lifting and punching steps are illustrated in FIG. 4b.

The silicone diaphragm 84 along with the housing 90 and polyurethane layer 94 are removed from the teflon mold. The bottom edge of the shell area 86 is filled in prior to removal from the mold and the lower edge is trimmed.

Figures 4C, 4D:
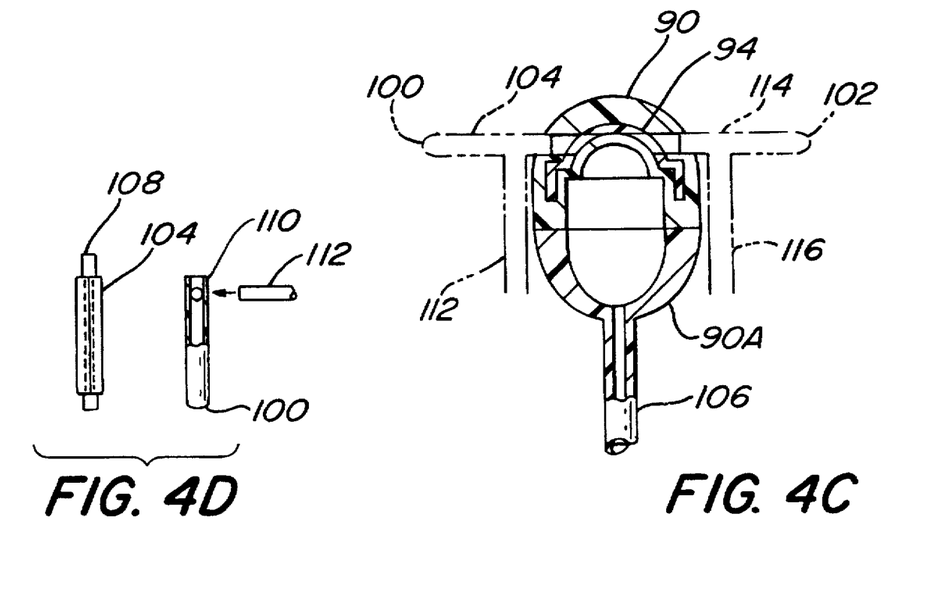

The operating catheter is mounted on a teflon mold and a medical grade silicone paste is coated over the ends of the catheter tubing and onto the mold. This yields a shaped end 90A attached to operating catheter 106. The lower portion of housing 90A is attached to housing 90 by suitable medical adhesive silicone type A.

The formation of the tubular members is briefly illustrated in FIG. 4D wherein the ends 100 and 102 are provided with rounded ends to prevent damage to the duct of the animal. In FIG. 4D, a tubular member 104 is mounted over a section of polyethylene tubing 108. The lower end of the tubing is dipped into 50% of the aforesaid medical adhesive silicone to produce the rounded lower portion 100. This may require trimming. Polyethylene tubing 108 is removed, hole 110 is punched into the tubing and a catheter 112 is attached by using the same medical adhesive silicone, type A. Tubular member 114 and catheter 116 are constructed in a similar manner. Both tubular members 104 and 114 are attached to housing 90, again using the same medical adhesive silicone.

It will be apparent to those skilled in the art that any variations are possible within the scope and spirit of the present invention. The medical adhesive silicone, type A, utilized in presently practicing the preferred invention is commercially available under the Trademark "SILASTIC" from Dow Corning Corporation of Midland, Mich. However, it will be readily apparent to those skilled in the art that other suitable materials may be utilized to fabricate an occluder in accordance with the present invention. The catheters utilized in practicing the present invention may be any suitable medical grade silicone tubing such as those commercially available from Baxter Health Care Corporation of McGaw Park, Ill. The polyurethane may be any suitable polyurethane such as that which is commercially available under the Trademark "SURETHANE" from Cardiac Control Systems, Inc., 3 Commerce Boulevard, Palm Coast, Fla., 32037.

Referring now to FIGS. 5, 5A, 6 and 6A, there are shown, inter alia, illustrations of some of the other alternate embodiments of the flexible member or diaphragm within the scope of the present invention.

Figures 5, 5A, 6:
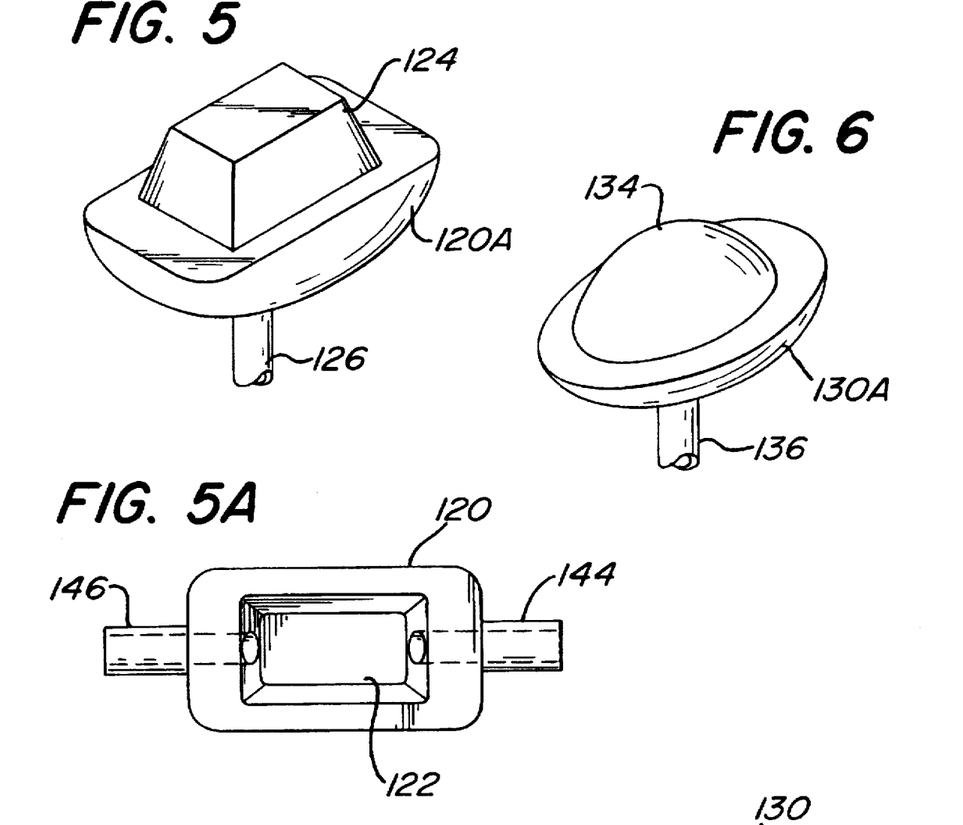
FIG. 5 is a view in perspective of another embodiment of the present invention illustrating a rectangular shaped diaphragm.
FIG. 5A is a bottom plan view looking up into the housing of the occluder utilized with the diaphragm of FIG. 5.
FIG. 6 is an isometric view of an occluding collector in accordance with the present invention illustrating an oval shaped diaphragm.

FIG. 5 illustrates a flexible member or diaphragm 124 which may be of a substantially rectangular or trapezoidal shape. Obviously, within the broad meaning of a rectangular shape, where four sides of the rectangle are equal, this becomes a square shape. FIG. 6 illustrates an embodiment of a flexible member or diaphragm 134 utilizing an oval shape. However, Applicant's invention is not limited to the specifics of an oval or trapezoidal shape, but it is apparent that some rounding of the corners of diaphragm 124 would produce a substantially cylindrical shape or substantial elongation of the oval or elliptical shape of flexible member or diaphragm 134 would also approach a substantially cylindrical shape. It is understood within the scope and spirit of the present invention, that Applicant is not limiting his invention to the specific details of the shape of the flexible member or diaphragm. It is also recognized that the flexible member or diaphragm could be of a substantially pyramidal shape having any suitable number of sides at its base, such as three, four, five or six. For example, a pyramidal shape with a three sided base would lend itself very appropriately to an embodiment wherein the input and output tubular members are 120° apart instead of 180° apart. However, as discussed above with respect to the hemispherical shape or round shape of FIGS. 1, 2 and 3, the input and output tubular members may be located any number of degrees apart including the 120° just referred to.

Referring further to FIGS. 5 and 6, there is shown in FIG. 5 the lower portion of the housing 120A and the operating catheter 126. Flexible member 124 is shown in the closed position or the condition wherein an operating fluid is applied via operating catheter 126.

Referring to FIG. 5A, FIG. 5A is a bottom plan view of the upper portion of housing 120 illustrating the biological fluid passageway 122, first tubular member 144 and second tubular member 146. First tubular member 144 may be referred to as the input tubular member and tubular member 146 may be referred to as the output tubular member, or vice versa depending upon the way it is inserted into a biological duct. The collecting and flush catheters are not illustrated in FIG. 5A and 6A, although it is understood that they would be present with their lumens in communication with the tubular members 144 and 146 in the case of FIG. 5A and in communication with the lumens of tubular members 154 and 156 in the case of FIG. 6A.

Figure 6A:
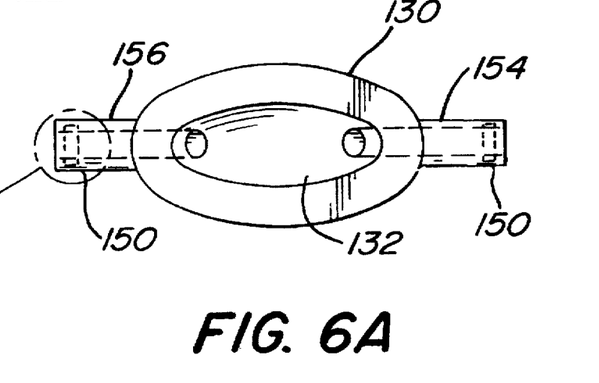
FIG. 6A is a bottom plan view looking up into the housing of an occluder utilized with the diaphragm of FIG. 6.

Referring now to FIGS. 6 and 6A, elliptical or ellipsoid flexible member 134 is shown formed on the lower portion of the housing 130A. The upper portion of the housing is shown in FIG. 6A at 130. The flexible member or diaphragm 134 may be operated by an operating fluid supplied via operating catheter 136. The biological fluid passageway is shown on FIG. 6A at 132.

Figure 6B:
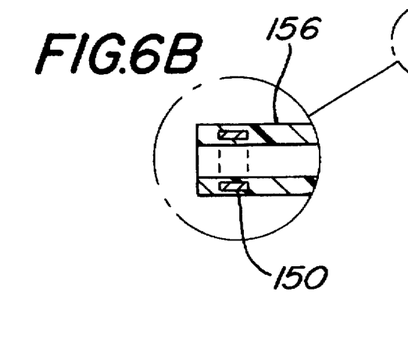
FIG. 6B is an enlarged cross sectional view of the circled area in FIG. 6A.

In all of the embodiments a radiopaque material may be provided in the housing or tubular members to enable visualization of the occluding collector by means of X-ray equipment. This is not required, but it provides a significant advantage of being able to monitor without surgery the position of the occluding collector. An example of providing the radiopaque material is shown in FIG. 6A and the exploded view of FIG. 6B wherein a metallic ring 150, such as a stainless steel ring is embedded within the walls of the tubular members 156 and 154. However, the ring need not be metallic, but may be made of any radiopaque material such as various fillers and the like. Furthermore, the entire housing and tubular members may be provided with a radiopaque filler, such radiopaque fillers being commercially available. However, a presently preferred embodiment would be to embed rings of radiopaque material within the walls of the tubular members.

Referring now to FIG. 7, there is shown another embodiment of the present invention wherein the structure of housing 150, diaphragm or flexible member 154, operating catheter 156 and the other structure, other than the tubular members, may be the same as or similar to any of the other embodiments. However, FIG. 7 illustrates the use of a suture or ligature ring 160 on tubular member 158. Tubular member 162 would be provided with a similar ligature ring. Although use of ligature rings on the tubular members is not a presently preferred embodiment, it has been found to provide a suitable structure for the tubular members which may provide a means of more securely installing or implanting the tubular member into a biological fluid duct wherein the ligature ring 160 is inserted into the duct and a ligature is tied around the duct over tubular member 158 approximately in the location 164. In other words, a ligature similar to that shown at 28 in FIG. 1 would be tied around the outside of the biological fluid duct where a tubular member has been inserted and the ligature would be tied at a location shown approximately at 164 or, in other words between ligature ring 160 and catheter 166.

In view of the above, it would be apparent to those skilled in the art that various modifications may be made to the teachings herein within the scope and spirit of the present invention. Various shapes and forms of flexible members or diaphragms may be utilized. Variations may be made in the shell and/or tubular members including providing tubular members of various lengths. Various other materials may be utilized in the fabrication, including non-medical grade silicone, polyurethane or the like. The arrangement of the catheters may be located at various other positions or locations other than those illustrated. The several catheters may be combined into one multi-lumen catheter. The apparatus of the present invention may be utilized without access ports wherein the catheter ends are exteriorized through the skin. However, presently preferred embodiments and methods have been disclosed.

In view of the above, the present invention may be embodied in other specific forms without departing from the spirit or essential attributes thereof and, accordingly, reference should be made to the appended claims, rather than to the foregoing specification as indicating the scope of the invention.

We claim:

1. An implantable occluding apparatus, comprising:
   a housing having a biological fluid passageway between and connected to a first and second tubular members adapted to be inserted into a duct carrying a biological fluid;
   a flexible member mounted within said biological fluid passageway within said housing, said flexible member being deflectable in response to pressure of an operating fluid to close said biological fluid passageway;
   a first catheter connected to said housing for supplying said operating fluid for deflection of said flexible member; and
   a second catheter, a lumen of said second catheter being in communication with a lumen of one of said tubular members.

2. An apparatus in accordance with claim 1 including a third catheter, a lumen of the third catheter being in communication with a lumen of the other of said tubular members.

3. An apparatus in accordance with claim 1 wherein said housing is constructed of silicone.

4. An apparatus in accordance with claim 3 wherein said housing is provided with a layer of material against which said flexible member comes in contact upon being deflected in response to the pressure of said fluid, said layer of material having a surface of low adhesion.

5. An apparatus in accordance with claim 4 wherein said layer of material is comprised of polyurethane.

6. An apparatus in accordance with claim 1 including an access port connected to a free end of said first catheter.

7. An apparatus in accordance with claim 1 including an access port connected to a free end of said second catheter.

8. An apparatus in accordance with claim 1 wherein said flexible member is a diaphragm.

9. An apparatus in accordance with claim 8 wherein said diaphragm has a periphery which is substantially circular.

10. An apparatus in accordance with claim 9 wherein said diaphragm has a diameter of about 2 to 4 millimeters.

11. An apparatus in accordance with claim 8 wherein said diaphragm has a periphery which is substantially oval.

12. An apparatus in accordance with claim 8 wherein said diaphragm has a periphery which is substantially rectangular.

13. An apparatus in accordance with claim 1 wherein a radiopaque material is embedded therein.

14. An apparatus in accordance with claim 1 wherein said first and second tubular members are provided with ligature rings.

15. An apparatus for collecting a biological fluid, comprising:

a housing having a first tubular member and a second tubular member and a biological passageway connecting said first and second tubular members, said first and second tubular members being adapted to be inserted into a duct carrying a biological fluid;

a diaphragm mounted within said housing, said diaphragm being deflectable to a convex condition in response to pressure of a fluid to close said biological passageway, said diaphragm being retracted to a concave condition in response to suction of fluid to open said biological passageway, said diaphragm remaining in said convex condition once pressure has been applied until a suction force is applied to said diaphragm;

a first catheter connected to said housing for supplying said fluid for applying pressure or suction to said diaphragm; and a second catheter, a lumen of said second catheter being in communication with a lumen of one of said tubular members.

16. An apparatus in accordance with claim 15 including a third catheter, a lumen of said third catheter being in communication with a lumen of the other of said tubular members.

17. An apparatus in accordance with claim 15 wherein said first and second tubular members are provided with rounded ends.

18. An apparatus in accordance with claim 15 wherein said housing is constructed of silicone.

19. An apparatus in accordance with claim 15 wherein said housing is provided with a layer of material against which said diaphragm comes in contact upon being deflected in response to the pressure of said fluid, said layer of material having a surface of low adhesion.

20. An apparatus in accordance with claim 19 wherein said layer of material is comprised of polyurethane.

21. An apparatus in accordance with claim 15 including an access port mounted on the free end of at least one of said catheters.

22. An apparatus in accordance with claim 15 wherein said diaphragm has a periphery which is substantially circular.

23. An apparatus in accordance with claim 15 wherein said apparatus includes radiopaque material for visualization during an X-ray procedure.

24. An apparatus in accordance with claim 15 wherein said first tubular member and said second tubular member are provided with ligature rings.

25. A method of collecting bile in an animal, comprising the steps of:

implanting a housing having a biological passageway between and connected to a first and a second tubular member such that said first and second tubular members are inserted into the common bile duct;

selectively operating a flexible member mounted within said housing utilizing pressure of a fluid delivered via a first catheter from a subdermal access port; and collecting bile via a second catheter which communicates with a lumen of one of said tubular members closest to a gall bladder of the animal, said second catheter being in communication with a second subdermal access port.

26. A method in accordance in claim 25 wherein said flexible member is a diaphragm and said operating step includes the steps of applying pressure to said diaphragm wherein said diaphragm remains in the closed position or applying suction to said diaphragm wherein said diaphragm will remain in the open position.

* * * * *